US010857319B2

United States Patent
D'Angelo et al.

(10) Patent No.: US 10,857,319 B2
(45) Date of Patent: Dec. 8, 2020

(54) MEASURING CONTINUITY OF THERAPY ASSOCIATED WITH A RESPIRATORY TREATMENT DEVICE

(75) Inventors: Mark Dominic D'Angelo, Harrison City, PA (US); Benjamin Irwin Shelly, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 838 days.

(21) Appl. No.: 13/976,038

(22) PCT Filed: Jan. 5, 2012

(86) PCT No.: PCT/IB2012/050055
§ 371 (c)(1),
(2), (4) Date: Jun. 26, 2013

(87) PCT Pub. No.: WO2012/095764
PCT Pub. Date: Jul. 19, 2012

(65) Prior Publication Data
US 2013/0340751 A1    Dec. 26, 2013

Related U.S. Application Data

(60) Provisional application No. 61/432,804, filed on Jan. 14, 2011.

(51) Int. Cl.
*A61M 16/00*    (2006.01)

(52) U.S. Cl.
CPC .... *A61M 16/0051* (2013.01); *A61M 16/0057* (2013.01); *A61M 2016/0027* (2013.01);
(Continued)

(58) Field of Classification Search
CPC .......... A61M 16/0051; A61M 16/0057; A61M 2205/50; A61M 2205/583; A61M 2016/0039; A61M 2205/505; A61M 2205/52; A61M 2205/581; A61M 2016/0027; A61M 16/024; F04C 2270/041
(Continued)

(56) References Cited

U.S. PATENT DOCUMENTS

| | | | | |
|---|---|---|---|---|
| 5,517,983 A | * | 5/1996 | Deighan | A61M 16/00 128/204.21 |
| 7,890,342 B1 | * | 2/2011 | Yruko | A61M 16/0051 705/2 |
| 2008/0078384 A1 | | 4/2008 | Messenger | |

FOREIGN PATENT DOCUMENTS

| CN | 1713850 A | 12/2005 |
|---|---|---|
| CN | 1816302 A | 8/2006 |

(Continued)

*Primary Examiner* — Timothy A Stanis
*Assistant Examiner* — Victoria Murphy

(57) ABSTRACT

Continuity of therapy associated with a respiratory treatment device may be measured. Information relating to therapy administered via the respiratory treatment device to a subject during a therapy session may be received. Based on the received information, a quantity of therapy interruption events that occurred during the therapy session may be determined. A continuity indicator may be determined based on the quantity of therapy interruption events that occurred during the therapy session. The continuity indicator is indicative of continuity of therapy associated with the respiratory treatment device during the therapy session.

21 Claims, 3 Drawing Sheets

(52) U.S. Cl.
CPC . *A61M 2016/0039* (2013.01); *A61M 2205/50* (2013.01); *A61M 2205/505* (2013.01); *A61M 2205/52* (2013.01); *A61M 2205/581* (2013.01); *A61M 2205/583* (2013.01); *F04C 2270/041* (2013.01)

(58) Field of Classification Search
USPC .............................................. 705/2; 600/301
See application file for complete search history.

(56) References Cited

FOREIGN PATENT DOCUMENTS

| | | | |
|---|---|---|---|
| CN | 101203260 | A | 6/2008 |
| CN | 101500633 | A | 8/2009 |
| CN | 101588832 | A | 11/2009 |
| WO | WO9916492 | A1 | 4/1999 |
| WO | WO2008138040 | A1 | 11/2008 |
| WO | WO2010121313 | A1 | 10/2010 |

* cited by examiner

MEASURING CONTINUITY OF THERAPY ASSOCIATED WITH A RESPIRATORY TREATMENT DEVICE

CROSS-REFERENCE TO RELATED APPLICATIONS

This patent application claims the priority benefit under 35 U.S.C. § 371 of international patent application no. PCT/IB2012/050055, filed Jan. 5, 2012, which claims the priority benefit under 35 U.S.C. § 119(e) of U.S. Provisional Application No. 61/432,804 filed on Jan. 14, 2011, the contents of which are herein incorporated by reference.

BACKGROUND OF THE INVENTION

1. Field of the Disclosure

This disclosure relates to measuring continuity of therapy associated with a respiratory treatment device.

2. Description of the Related Art

It is known to treat a medical disorder or to diagnose, treat, or monitor the condition of a subject using medical equipment. For example, subjects suffering from a pulmonary or respiratory disorder, such as obstructive sleep apnea (OSA), are often treated with a pressure support device. One example of such a pressure support device is a continuous positive airway pressure (CPAP) device. A CPAP device delivers a flow of fluid to the airway of the subject throughout the subject's breathing cycle in order to "splint" the airway, thereby preventing its collapse during sleep.

Another example of a pressure support device provides a bi-level positive pressure therapy, in which the pressure of fluid delivered to the subject's airway varies or is synchronized with the subject's breathing cycle to maximize the medical effect and/or comfort to the subject. This type of device may be known as a bi-level positive airway pressure (BiPAP) device. With some BiPAP devices, a lower pressure is delivered to the subject during the subject's expiratory phase than during the inspiratory phase. It is also known to provide an auto-titration positive pressure therapy in which the pressure provided to the subject changes based on detected conditions of the subject. Such detected conditions may include whether the subject is snoring or experiencing an apnea, hypopnea, or upper airway resistance.

In treating a subject using any of the above-described pressure support systems, each of which represents a mode of providing pressure support, it is often desirable to monitor various parameters associated with the use of such systems. Once a subject is diagnosed with a breathing disorder, he or she is typically prescribed a pressure support therapy, i.e., a mode of pressure support (e.g., continuous, bi-level, or auto-titration), and given a prescribed pressure support level. The pressure support therapy (mode of pressure support and pressure settings) is typically prescribed by a physician after the subject undergoes a sleep study at a sleep lab. The subject's healthcare provider, such as that subject's physician or health insurance company, is often interested in ensuring that the subject actually uses the pressure support therapy as prescribed. Thus, it is known to monitor a subject's compliance with the prescribed therapy by monitoring the subject's usage of the pressure support device.

Typically, a doctor or other health care provider is able to track and monitor certain aspects of the operation of the prescribed pressure support device. These aspects are typically limited to whether the device is off or on, and/or the parameters of the pressurized gas (e.g., pressure, flow, etc.) delivered by the device. Other conventional compliance monitoring systems may provide information on respiratory events experienced by the subject (e.g., apneas and hypopneas,). A device may include a timer that determines the amount of time the device has been on and/or generating a pressurized flow of breathable gas. Often, the monitoring systems will show times where the patient is connected and times when the patient is not connected. The device may be configured to transmit this information from the device to a remote computer to facilitate observation by a doctor or other health care provider. The present inventor recognized that this information may not, however, provide a complete understanding of the effectiveness of the therapy provided to the subject.

SUMMARY OF THE INVENTION

Accordingly, it is an object of the present invention to provide a method of monitoring the usage of a medical device that overcomes the shortcomings of conventional monitoring method. This object is achieved according to one embodiment of the present invention by providing a method for measuring continuity of therapy associated with a respiratory treatment device. The method includes receiving information relating to therapy administered via the respiratory treatment device to a subject during a therapy session. The method includes determining, based on the received information, a quantity of therapy interruption events that occurred during the therapy session. The method further includes determining a continuity indicator based on the quantity of therapy interruption events that occurred during the therapy session. The continuity indicator is indicative of continuity of therapy associated with the respiratory treatment device during the therapy session.

Another aspect of the disclosure relates to a system for measuring continuity of therapy associated with a respiratory treatment device. The system includes a communications module, an interruption quantification module, and/or a continuity determination module. The communications module is configured to receive information relating to therapy administered via the respiratory treatment device to a subject during a therapy session. The interruption quantification module is configured to determine, based on the received information, a quantity of therapy interruption events that occurred during the therapy session. The continuity determination module is configured to determine a continuity indicator based on the quantity of therapy interruption events that occurred during the therapy session. The continuity indicator is indicative of continuity of therapy associated with the respiratory treatment device during the therapy session.

Yet another aspect of the disclosure relates to a system for measuring continuity of therapy associated with a respiratory treatment device. The system includes a communication means, an interruption quantification means, and/or a continuity determination means. The communication means is configured for receiving information relating to therapy administered via the respiratory treatment device to a subject during a therapy session. The interruption quantification means is configured for determining, based on the received information, a quantity of therapy interruption events that occurred during the therapy session. The continuity determination means is configured for determining a continuity indicator based on the quantity of therapy interruption events that occurred during the therapy session. The continuity indicator is indicative of continuity of therapy associated with the respiratory treatment device during the therapy session.

These and other objects, features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the technology, the structural components illustrated herein are drawn to scale. It is to be expressly understood, however, that the drawings are for the purpose of illustration and description only and are not a limitation of the technology. In addition, it should be appreciated that structural features shown or described in any one embodiment herein can be used in other embodiments as well. It is to be expressly understood, however, that the drawings are for the purpose of illustration and description only and are not intended as a definition of the limits of the technology.

DETAILED DESCRIPTION OF EXEMPLARY EMBODIMENTS

Figure 1:
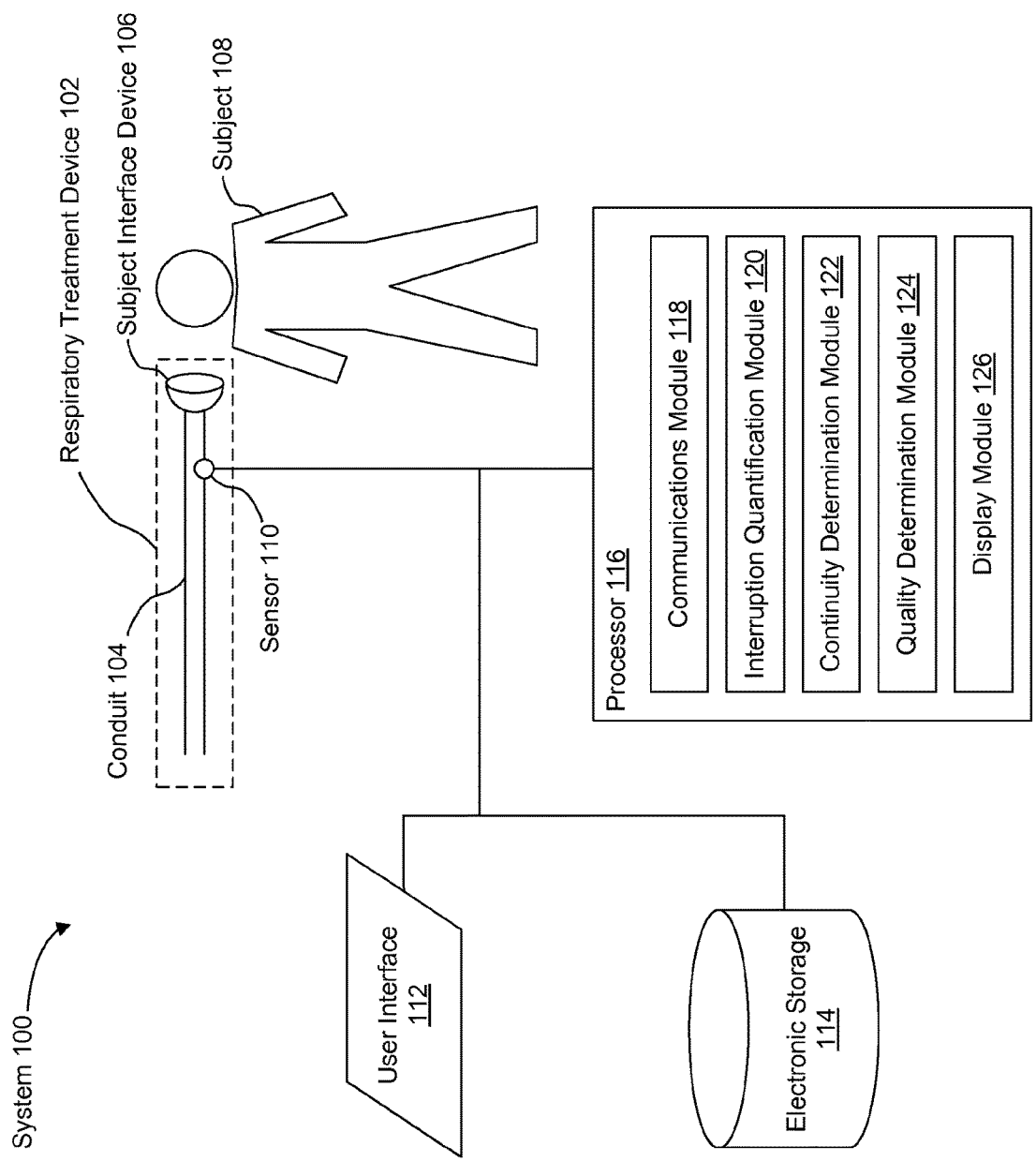
FIG. 1 illustrates a system for measuring continuity of therapy associated with a respiratory treatment device, in accordance with one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Exemplary embodiments solve or greatly alleviate one or more deficiencies of conventional compliance monitoring approaches associated with pulmonary or respiratory disorder therapies. More specifically, some embodiments of the present invention contemplate quantifying and incorporating interruption events (e.g., disconnects from the device, ramp-button presses, times shutting the device off and turning it back on, and/or other interruption events) into an indicator reflecting the continuity of therapy. Such an indicator may include a quantitative value (e.g., an index, a number of events, and/or other quantitative values) and/or a qualitative value (e.g., plus/minus indicator, good/bad indicator, thumbs-up/thumbs-down, happy/sad face, green/red indicator, and/or other qualitative values). Clinicians can use this information to differentiate subjects who struggle with using the therapy from subjects who successfully use a treatment device and sleep all night long.

Providing an indicator that reflects the "continuity of therapy" helps to provide more complete data on how likely a subject is to continue with a prescribed therapy and can provide an early indicator for a clinician to intervene with follow-up education, alternative interfaces, alternative therapy options, and/or other remedies for inadequate therapy. It is noteworthy that, while exemplary embodiments are described herein in the context of usage with pressure support devices (e.g., CPAP, BiPAP, and/or other pressure support devices), some embodiments may be suitable for other respiratory treatment devices that require subject adherence. For example, some embodiments may be implemented with therapies involving use of mandibular advancement devices.

FIG. 1 illustrates a system 100 for measuring continuity of therapy associated with a respiratory treatment device 102, in accordance with one or more embodiments. In an exemplary embodiment, respiratory treatment device 102 includes a pressure support device (e.g., CPAP, BiPAP, and/or other pressure support devices), a mandibular advancement device, and/or other devices configured to treat pulmonary or respiratory disorders. As depicted in FIG. 1, respiratory treatment device 102 includes a conduit 104 coupled with a subject interface device 106 for delivering a flow of gas from a pressure generating system (not shown) to a subject 108, and/or other components. A sensor 110 is coupled with conduit 104, the pressure generating system, and/or subject interface device 106.

The present invention further contemplates that system 100 includes a user interface 112, electronic storage 114, a processor 116, and/or other components. In some embodiments, user interface 112, electronic storage 114, and/or processor 116 is included within the respiratory treatment device 102 or may be included in system 100 as separate components.

Subject interface device 106 in fluid communication with a source of a respiratory gas or other breathable substance (not shown). For example, a flow of breathable gas may be delivered to subject 108 through conduit 104 having one or more parameters that are controlled in accordance with a therapy regime. The one or more parameters of the flow of breathable gas that are controlled may include one or more of pressure, flow rate, volume, composition, humidity, temperature, and/or other parameters.

Subject interface device 106 is in fluid communication with one or more orifices of the airway of subject 108 in a sealed or unsealed manner. Some examples of subject interface device 106 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present technology is not limited to these examples, and contemplates implementation of any subject interface.

As noted above, sensor 110 is configured to generate output signals conveying information relating to therapy administered via respiratory treatment device 102 to subject 108 during a therapy session. A therapy session may include a single period of therapy (e.g., a single night), a portion of a period of therapy (e.g., three hours during a night), and/or a series of periods of therapy (e.g., several nights). By way of non-limiting example, information relating to therapy administered via respiratory treatment device 102 to subject 108 during a therapy session may include interactions with the respiratory treatment device by the subject 108 (e.g., turning therapy on or off, pressing the ramp button, and/or other input to the device), connects/disconnects from respiratory treatment device 102 by the subject, and/or information indicative thereof (e.g., leak, total airflow, subject airflow, and/or other device performance metrics), and/or other information relating to the therapy. In some embodiments, sensor 110 may include a flow meter, a capnometer, a pressure sensor, a motor-speed sensor, a motor-current sensor, a thermistor, and/or other sensors. The present disclosure is not limited to these examples, and contemplates implementation of any sensor.

It will be appreciated that the illustration of sensor 110 in FIG. 1 as a single component is not intended to be limiting. In one embodiment, sensor 110 includes a plurality of sensors. Further, the location of the sensor 110 relative to the conduit 104, the pressure generating system, and/or the subject interface device 106 is not intended to be limiting. In an exemplary embodiment, for example, sensor 110 is disposed in the pressure generating system and is a pressure sensor, flow sensor, or a combination thereof and detects the flow and/or pressure of the gas communicated to the patient via conduit 104 using conventional flow/pressure sensing techniques. Sensor 110 may include one or more sensing units disposed in the conduit 104, the subject interface device 106, at the source of the breathable substance (i.e., in the pressure generating system), and/or disposed at other locations in the system 100.

User interface 112 is configured to provide an interface between system 100 and a user (e.g., a subject, a caregiver, a therapy decision-maker, etc.) through which the user may provide information to and receive information from the system. This enables data, results, and/or instructions (e.g., turning therapy on or off, pressing the ramp button, and/or other instructions) and any other communicable items, collectively referred to as "information," to be communicated between the user and system 100. Examples of interface devices suitable for inclusion in user interface 112 include a keypad, buttons, switches, a keyboard, knobs, levers, a display screen, a touch screen, speakers, a microphone, an indicator light, an audible alarm, and a printer. According to various embodiments, the user interface may be co-located with the respiratory treatment device 102 and/or located remotely and accessible by a caregiver, a therapy decision-maker, etc.

It is to be understood that other communication techniques, either hard-wired or wireless, are also contemplated by the present technology as user interface 112. For example, the present technology contemplates that the user interface may be integrated with a removable storage interface provided by electronic storage 114. In this example, information may be loaded into the user interface from removable storage (e.g., a smart card, a flash drive, a removable disk, etc.) that enables the user(s) to customize the implementation of the user interface. Other exemplary input devices and techniques adapted for use with system 100 as user interface 112 include, but are not limited to, an RS-232 port, RF link, an IR link, modem (telephone, cable or other). In short, any technique for communicating information with system 100 is contemplated by the present technology as the user interface.

According to exemplary embodiments, electronic storage 114 includes electronic storage media that electronically stores information. The electronic storage media of electronic storage 114 may include one or both of system storage that is provided integrally (i.e., substantially non-removable) with system 100 and/or removable storage that is removably connectable to the system via, for example, a port (e.g., a USB port, a firewire port, etc.) or a drive (e.g., a disk drive, etc.). The electronic storage 114 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 114 may store software algorithms, information determined by the processor 116, information received via user interface 112, and/or other information that enables system 100 to function as described herein. Electronic storage 114 may be a separate component within system 100, or the electronic storage may be provided integrally with one or more other components of the system (e.g., processor 116).

Processor 116 is configured to provide information processing capabilities in system 100. As such, the processor may include one or more of a digital processor, an analog processor, a digital circuit designed to process information, an analog circuit designed to process information, a state machine, and/or other mechanisms for electronically processing information. Although processor 116 is shown in FIG. 1 as a single entity, this is for illustrative purposes only. In some implementations, processor 116 may include a plurality of processing units. These processing units may be physically located within the same device, or the processor may represent processing functionality of a plurality of devices operating in coordination.

As is shown in FIG. 1, processor 116 is configured to execute one or more computer program modules. The present invention contemplates that one or more computer program modules include one or more of a communications module 118, an interruption quantification module 120, a continuity determination module 122, a quality determination module 124, a display module 126, and/or other modules. Processor 116 may be configured to execute modules 118, 120, 122, 124, and/or 126 by software; hardware; firmware; some combination of software, hardware, and/or firmware; and/or other mechanisms for configuring processing capabilities on the processor.

It should be appreciated that although modules 118, 120, 122, 124, and 126 are illustrated in FIG. 1 as being co-located within a single processing unit, in implementations in which processor 116 includes multiple processing units, one or more of modules 118, 120, 122, 124, and/or 126 may be located remotely from the other modules. The description of the functionality provided by the different modules 118, 120, 122, 124, and/or 126 described below is for illustrative purposes, and is not intended to be limiting, as any of modules 118, 120, 122, 124, and/or 126 may provide more or less functionality than is described. For example, one or more of the modules 118, 120, 122, 124, and/or 126 may be eliminated, and some or all of its functionality may be provided by other ones of the modules 118, 120, 122, 124, and/or 126. As another example, the processor 116 may be configured to execute one or more additional modules that may perform some or all of the functionality attributed below to one of the modules 118, 120, 122, 124, and/or 126.

Communications module 118 may be configured to receive information relating to therapy administered via respiratory treatment device 102 to subject 108 during a therapy session. Such information may be received via signals generated by sensor 110. Information received by communications module 118 is stored by electronic storage 114, and subsequently recalled by processor 116 (or modules thereof) for carrying out various operations described herein. In some embodiments, information received by communications module 118 is transmitted to remote computers to inform caregivers, therapy decision-makers, and/or others regarding therapy provided to subject 108.

As noted above, information relating to therapy administered via respiratory treatment device 102 to subject 108 during a therapy session may include interactions with the respiratory treatment device by subject 108 (e.g., turning therapy on or off, pressing the ramp button, and/or other input to the device), connects/disconnects from the respiratory treatment device 102 by the subject, and/or information indicative thereof (e.g., leak, total airflow, subject airflow, and/or other device performance metrics), and/or other information relating to the therapy. Some or all of the information received by the communications module may be provided to user interface 112 for presentation to a user.

Interruption quantification module 120 may be configured to determine, based on information received by communications module 118, a quantity and/or timing of therapy interruption events that occurred during the therapy session. By way of non-limiting example, a therapy interruption event may include respiratory treatment device 102 being turned off or on, a ramp sequence of the respiratory treatment device 102 being engaged, the respiratory treatment device being disconnected from the subject, and/or other events that interrupt therapy administered to the subject during the therapy session. Determining the timing of a therapy interruption event may include determining a beginning time, an end time, a duration, a time period between events, and/or other timing parameters associated with the therapy interruption event(s).

According to some embodiments, two or more successive therapy interruption events that occur within a predetermined period of time may be considered a single therapy interruption event, for quantification purposes, by interruption quantification module 120. An example of this may include a subject turning the respiratory treatment device 102 off, back on again, and then pressing the ramp button. This sequence, if it occurs within a given period of time (e.g., five minutes), may be considered a single interruption in therapy.

Continuity determination module 122 is configured to determine a continuity indicator based on the quantity and/or timing of therapy interruption events that occurred during the therapy session. The present invention contemplates, in an further exemplary embodiment, that continuity determination module 122 is further configured to determine the continuity indicator based on a duration of the therapy session. The continuity indicator is indicative of continuity of therapy associated with the respiratory treatment device during the therapy session. The continuity indicator may include one or more quantitative values and/or a qualitative values. Determining the continuity indicator may include determining the number of times therapy is interrupted in a given amount of time, determining the timing of individual ones of the interruption events within the given amount of time, and/or other metrics related to the administered therapy.

One exemplary embodiment of the present invention contemplates counting the number of interruption events per hour and averaging that number across a therapy session. Inputs factored into the continuity indicator may include, for example, times of on/off button presses, times of ramp button press, times of other user input to respiratory treatment device 102 (e.g. through a button press or other user interface 112 interaction). Additionally, values such as leak, total airflow, or subject airflow, which may be used to determine whether subject 108 has connected or disconnected respiratory treatment device 102, may be factored into the continuity indicator, in some embodiments. It is noteworthy that, in some embodiments, continuity determination module 122 may be configured to provide the continuity indicator to one or more components of system 100 to affect the therapy delivered to the subject 108, as described in connection with FIG. 3.

The present invention contemplates that quality determination module 124 is configured to determine a therapy quality indicator. The therapy quality indicator is indicative of an effectiveness of the therapy administered via respiratory treatment device 102 to subject 108 during the therapy session. The present invention contemplates that the therapy quality indicator is determined based on the continuity indicator obtained via continuity determination module 122 and one or more other values. The therapy quality indicator may include one or more quantitative values and/or qualitative values.

According to some embodiments, determining the therapy quality indicator is based on the continuity indicator and one or more of an apnea-hypopnea index (AHI); a respiratory disturbance index (RDI); an arousal index (or spontaneous arousal index); a duration of the therapy session; information related to one or more of apnea, hypopnea, respiratory disturbance, arousal, or a duration of the therapy session; and/or other indexes or information relating to the therapy session. One or more of the aforementioned indexes and/or types of information may be determined by quality determination module 124, by one or more other module(s) described herein, and/or by a remote computer. In is noteworthy that, in some embodiments, quality determination module 124 may be configured to provide the therapy quality indicator to one or more components of system 100 to affect the therapy delivered to subject 108, as described in connection with FIG. 3.

The apnea-hypopnea index may be described as an index of severity that combines apneas and hypopneas, which gives an overall severity of sleep apnea including sleep disruptions and desaturations (i.e., a low level of oxygen in the blood). The apnea-hypopnea index may be calculated by dividing the number of apneas and hypopneas by the number of hours of sleep. Apnea-hypopnea index values are typically categorized as 5-15 being considered "mild," 15-30 being considered "moderate," and above 30 being considered "severe." The respiratory disturbance index is similar to the apnea-hypopnea index, however, it may also include respiratory events that do not technically meet the definitions of apneas or hypopneas, but do disrupt sleep. The respiratory disturbance index may be calculated by may be calculated by dividing the sum of apneas, hypopneas, and other respiratory events by the number of hours of sleep. The arousal index may be described as the number of spontaneous arousals (e.g. arousals not related to respiratory events, limb movements, snoring, etc.) divided by the number of hours of sleep. Determination of the arousal index may weight arousals based on duration and/or other parameters.

In some embodiments, the therapy quality indicator may be determined by quality determination module 124 based on the continuity indicator, an average therapy session duration, and an apnea-hypopnea index (or information related to apnea and/or hypopnea). The therapy quality indicator may indicate a first state (e.g., "good") responsive to the average therapy session duration breaching a first threshold, the apnea-hypopnea index (or information related to apnea and/or hypopnea) breaching a second threshold, and the continuity indicator breaching a third threshold. Otherwise, the therapy quality indicator may indicate a second state (e.g., "poor").

The present invention contemplates that display module 126 is configured to provide, for presentation to a user (e.g., a subject, a caregiver, a therapy decision-maker, etc.), the continuity indicator, the therapy quality indicator, values derived from or related to the continuity indicator and/or the therapy quality indicator, and/or other information associated with a therapy session of subject 108. Such information may be presented via user interface 112 or other mechanism for conveying information to the user.

Figure 2:
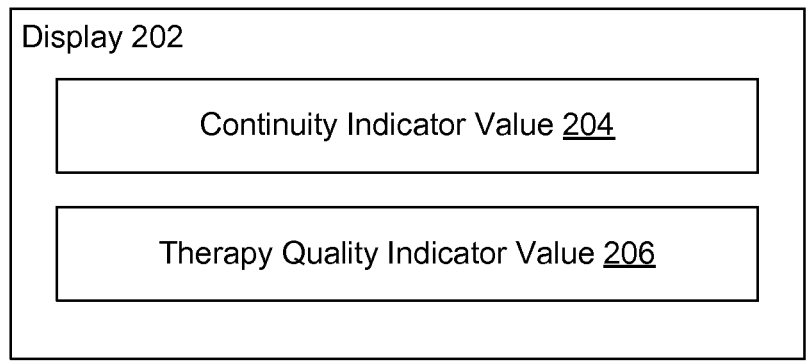
FIG. 2 illustrates a display for conveying, among other information, a continuity indicator and/or a therapy quality indicator, in accordance with one or more embodiments.

FIG. 2 illustrates an exemplary and non-limiting embodiment of a display 202 for conveying, among other information, a continuity indicator and/or a therapy quality indicator, in accordance with one or more embodiments of the present invention. As depicted, display 202 shows a continuity indicator value 204 and a therapy quality indicator value 206. Information presented by display 202 may be in a variety of forms such as graphical, numerical, or other forms of data representation. According to various embodiments, display 202 may be included in user interface 112 and/or a remote computer.

Figure 3:
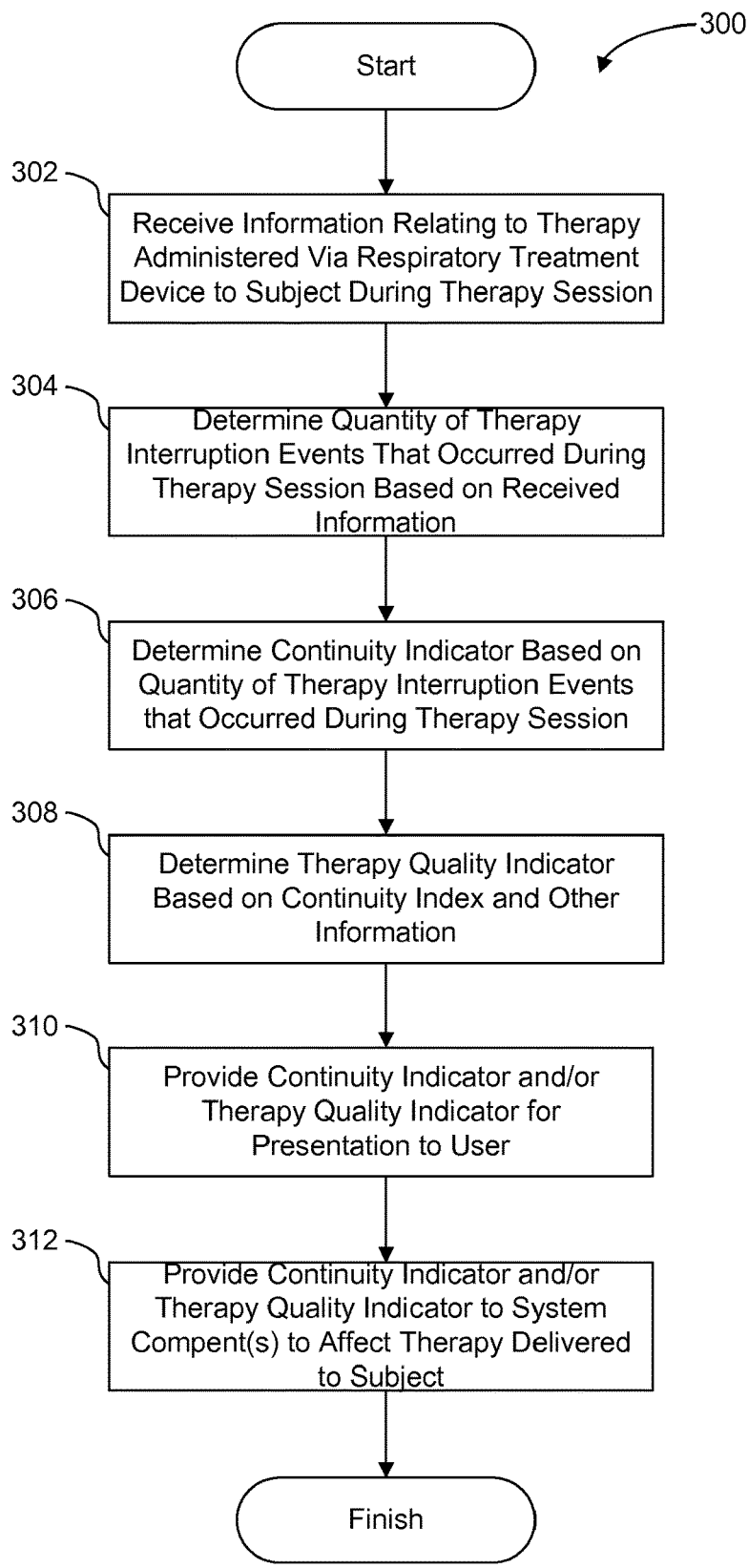
FIG. 3 is a flow chart illustrating a method for measuring continuity of therapy associated with a respiratory treatment device, in accordance with one or more embodiments.

FIG. 3 is a flow chart illustrating a method 300 for measuring continuity of therapy associated with a respiratory treatment device, in accordance with one or more embodiments. The operations of method 300 presented below are intended to be illustrative. In some implementations, method 300 may be accomplished with one or more additional operations not described, and/or without one or more of the operations discussed. Additionally, the order in which the operations of method 300 are illustrated in FIG. 3 and described below is not intended to be limiting.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, information relating to therapy administered via a respiratory treatment device to a subject during a therapy session is received. Such information may be included in signals received from sensor 110. In some embodiments, communications module 118 may perform operation 302.

At an operation 304, a quantity of therapy interruption events that occurred during the therapy session is determined based on the information received at operation 302. The timing of such therapy interruption events may be determined at operation 304. In some embodiments, two or more successive therapy interruption events that occur within a predetermined period of time may be considered a single therapy interruption event. Interruption quantification module 120 may perform operation 304, in accordance with some embodiments.

At an operation 306, a continuity indicator is determined based on the quantity of therapy interruption events that occurred during the therapy session and/or the timing of such therapy interruption events, as determined at operation 304. The continuity indicator is indicative of continuity of therapy associated with the respiratory treatment device during the therapy session. In some embodiments, determining the continuity indicator may be further based on a duration of the therapy session. Continuity determination module 122 may perform operation 306 in various embodiments.

At an operation 308, a therapy quality indicator is determined. The therapy quality indicator is indicative of an effectiveness of the therapy administered via the respiratory treatment device to the subject during the therapy session. In some embodiments, determining the therapy quality indicator may be based on the continuity indicator and one or more of an apnea-hypopnea index, a respiratory disturbance index, an arousal index, or a duration of the therapy session. According to various embodiments, determining the therapy quality indicator may be based on the continuity indicator, an average therapy session duration, and an apnea-hypopnea index. The therapy quality indicator may indicate a first state responsive to the average therapy session duration breaching a first threshold, the apnea-hypopnea index breaching a second threshold, and the continuity indicator breaching a third threshold. In one or more embodiments, quality determination module 124 may perform operation 308.

At an operation 310, the continuity indicator and/or the therapy quality indicator are provided for presentation to a user (e.g., a subject, a caregiver, a therapy decision-maker, etc.). In some embodiments, values derived from or related to the continuity indicator and/or the therapy quality indicator, and/or other information associated with a therapy session of subject 108 may be provided for presentation to a user at operation 310. Such information may be presented via user interface 112 or other mechanism for conveying information to the user. Display module 126 may perform operation 310, in accordance with some embodiments.

At an operation 312, the continuity indicator and/or the therapy quality indicator may be provided to one or more components of system 100 to affect the therapy delivered to subject 108. According to some embodiments, if an acceptable continuity indicator and/or quality indicator was observed over a period of time, but then worsened as the therapy delivered to the subject was changed or adjusted, the delivered therapy may revert, at least temporarily, to that at which the acceptable continuity indicator and/or quality indicator was observed. To illustrate, by way of non-limiting example, the subject 108 may use a CPAP device that ramps day by day from 4 to 5 to 6 to 7 centimeters of water ($cmH_2O$) with the end goal of reaching a prescription pressure of 10 $cmH_2O$. If the continuity indicator and/or the therapy quality indicator is good at 8 $cmH_2O$, but begins to drop off at 9 $cmH_2O$, then the pressure for the next session may revert to 8 $cmH_2O$ for one or more successive therapy sessions. In some embodiments, continuity determination module 122 and/or the quality determination module 124 may perform operation 312.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the technology has been described in detail for the purpose of illustration based on what is currently considered to be the most practical and preferred embodiments, it is to be understood that such detail is solely for that purpose and that the technology is not limited to the disclosed embodiments, but, on the contrary, is intended to cover modifications and equivalent arrangements that are within the spirit and scope of the appended claims. For example, it is to be understood that the present technology contemplates that, to the extent possible, one or more features of any embodiment can be combined with one or more features of any other embodiment.

The invention claimed is:

1. A method for measuring continuity of therapy associated with a respiratory treatment device with a system including one or more processors, the method comprising:
    receiving, with the one or more processors, information relating to therapy administered via the respiratory treatment device to a subject during a therapy session, the therapy session being a single period of therapy during which the respiratory treatment device is operating continuously;
    determining, with the one or more processors, based on the received information, a quantity of therapy interruption events that occurred during the therapy session, the therapy interruption events indicating events that interrupt therapy administered to the subject during the therapy session, wherein a therapy interruption event includes one or more of, a ramp sequence of the respiratory treatment device being engaged during the therapy session, or the respiratory treatment device being disconnected from the subject during the therapy session; and
    determining, with the one or more processors, a continuity indicator based on the quantity of therapy interruption events that occurred during the therapy session, the continuity indicator indicative of continuity of therapy associated with the respiratory treatment device during the therapy session.

2. The method of claim 1, wherein two or more successive therapy interruption events that occur within a predetermined period of time are considered a single therapy interruption event.

3. The method of claim 1, further comprising providing, with the one or more processors, the continuity indicator for presentation via an interface device.

4. The method of claim 1, further comprising determining, with the one or more processors, a therapy quality indicator, the therapy quality indicator being indicative of an effectiveness of the therapy administered via the respiratory treatment device to the subject during the therapy session, wherein:
    determining the therapy quality indicator is based on the continuity indicator and information related to one or more of apnea, hypopnea, respiratory disturbance, arousal, or a duration of the therapy session; or
    determining the therapy quality indicator is based on the continuity indicator, an average therapy session duration, and information related to apnea and/or hypopnea, and wherein the therapy quality indicator indicates a first state responsive to the average therapy session duration breaching a first threshold, the information related to apnea and/or hypopnea breaching a second threshold, and the continuity indicator breaching a third threshold.

5. The method of claim 4, further comprising utilizing, with the one or more processors, the continuity indicator and/or the therapy quality indicator to affect the therapy administered via the respiratory treatment device to the subject during the therapy session and/or a subsequent therapy session.

6. The method of claim 1, wherein the treatment device includes a conduit coupled with a subject interface device for delivering a flow of gas.

7. The method of claim 6, further comprising a sensor coupled with conduit and/or the subject interface device.

8. A system for measuring continuity of therapy associated with a respiratory treatment device, the system comprising one or more processors configured by machine-readable instructions to:
    receive information relating to therapy administered via the respiratory treatment device to a subject during a therapy session, the therapy session being a single period of therapy during which the respiratory treatment device is operating continuously;
    determine, based on the received information, a quantity of therapy interruption events that occurred during the therapy session, the therapy interruption events indicating events that interrupt therapy administered to the subject during the therapy session, wherein a therapy interruption event includes one or more of a ramp sequence of the respiratory treatment device being engaged during the therapy session, or the respiratory treatment device being disconnected from the subject during the therapy session; and
    determine a continuity indicator based on the quantity of therapy interruption events that occurred during the therapy session, the continuity indicator indicative of continuity of therapy associated with the respiratory treatment device during the therapy session.

9. The system of claim 8, wherein two or more successive therapy interruption events that occur within a predetermined period of time are considered a single therapy interruption event.

10. The system of claim 8, further comprising an interface device configured to present the continuity indicator.

11. The system of claim 8, wherein the one or more processors are further configured to determine a therapy quality indicator, the therapy quality indicator being indicative of an effectiveness of the therapy administered via the respiratory treatment device to the subject during the therapy session, wherein:
    determining the therapy quality indicator is based on the continuity indicator and information related to one or more of apnea, hypopnea, respiratory disturbance, arousal, or a duration of the therapy session; or
    determining the therapy quality indicator is based on the continuity indicator, an average therapy session duration, and information related to apnea and/or hypopnea, the therapy quality indicator indicating a first state responsive to the average therapy session duration breaching a first threshold, the information related to apnea and/or hypopnea breaching a second threshold, and the continuity indicator breaching a third threshold.

12. The system of claim 11, wherein the one or more processors are further configured to utilize the continuity indicator and/or the therapy quality indicator to affect the therapy administered via the respiratory treatment device to the subject during the therapy session and/or a subsequent therapy session.

13. The system of claim 8, wherein the treatment device includes a conduit coupled with a subject interface device for delivering a flow of gas.

14. The system of claim 13, further comprising a sensor coupled with conduit and/or the subject interface device.

15. A system for measuring continuity of therapy associated with a respiratory treatment device, the system comprising:
communication means configured for receiving information relating to therapy administered via the respiratory treatment device to a subject during a therapy session, the therapy session being a single period of therapy during which the respiratory treatment device is operating continuously;
interruption quantification means configured for determining, based on the received information, a quantity of therapy interruption events that occurred during the therapy session, the therapy interruption events indicating events that interrupt therapy administered to the subject during the therapy session, wherein a therapy interruption event includes one or more of a ramp sequence of the respiratory treatment device being engaged during the therapy session, or the respiratory treatment device being disconnected from the subject during the therapy session; and
continuity determination means configured for determining a continuity indicator based on the quantity of therapy interruption events that occurred during the therapy session, the continuity indicator indicative of continuity of therapy associated with the respiratory treatment device during the therapy session.

16. The system of claim 15, wherein two or more successive therapy interruption events that occur within a predetermined period of time are considered a single therapy interruption event.

17. The system of claim 15, further comprising interface means configured to present the continuity indicator.

18. The system of claim 15, further comprising quality determination means configured for determining a therapy quality indicator, the therapy quality indicator being indicative of an effectiveness of the therapy administered via the respiratory treatment device to the subject during the therapy session, wherein:
determining the therapy quality indicator is based on the continuity indicator and information related to one or more of apnea, hypopnea, respiratory disturbance, arousal, or a duration of the therapy session; or
determining the therapy quality indicator is based on the continuity indicator, an average therapy session duration, and information related to apnea and/or hypopnea, the therapy quality indicator indicating a first state responsive to the average therapy session duration breaching a first threshold, the information related to apnea and/or hypopnea breaching a second threshold, and the continuity indicator breaching a third threshold.

19. The system of claim 18, wherein the continuity determination means and/or the quality determination means is further configured to utilize the continuity indicator and/or the therapy quality indicator to affect the therapy administered via the respiratory treatment device to the subject during the therapy session and/or a subsequent therapy session.

20. The system of claim 15, wherein the treatment device includes a conduit coupled with a subject interface device for delivering a flow of gas.

21. The system of claim 20, further comprising a sensor coupled with conduit and/or the subject interface device.

* * * * *